United States Patent
Wårdell et al.

(10) Patent No.: US 6,629,973 B1
(45) Date of Patent: Oct. 7, 2003

(54) METHOD AND AN APPARATUS FOR CONTROLLED DESTRUCTION OF TISSUE

(75) Inventors: Karin Wårdell, Linköping (SE); Ola Eriksson, Linköping (SE); Gert Nilsson, Linköping (SE)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/889,449

(22) PCT Filed: Jan. 21, 2000

(86) PCT No.: PCT/SE00/00123
§ 371 (c)(1),
(2), (4) Date: Jul. 16, 2001

(87) PCT Pub. No.: WO00/42928
PCT Pub. Date: Jul. 27, 2000

(30) Foreign Application Priority Data

Jan. 25, 1999 (SE) ................................................. 9900202

(51) Int. Cl.[7] ............................................... A61B 18/18
(52) U.S. Cl. .............................. 606/40; 606/27; 606/32
(58) Field of Search ...................... 606/1–3, 10, 13–16, 606/32, 34, 41, 40; 600/300, 309, 310, 342; 607/88–89

(56) References Cited

U.S. PATENT DOCUMENTS 4,590,948 A * 5/1986 Nilsson ....................... 128/666
4,936,281 A 6/1990 Stasz
5,762,609 A * 6/1998 Benaron et al. ............. 600/473

FOREIGN PATENT DOCUMENTS

| SE | 508946 C2 | 11/1998 | |
| WO | WO 95/26678 A1 | 10/1995 | |
| WO | WO 97/17014 A1 | 5/1997 | |
| WO | WO 97/17014 | * 5/1997 | ............. A61B/5/02 |

* cited by examiner

Primary Examiner—Linda C. M. Dvorak
Assistant Examiner—Peter J Vrettakos
(74) Attorney, Agent, or Firm—Burns, Doane, Swecker & Mathis, L.L.P.

(57) ABSTRACT

The present invention relates to an apparatus for destroying a predetermined defined volume (10) in a tissue, such as generating controlled coagulation, so-called lesion, in the brain. More particularly, the apparatus comprises a main unit (1) for transmitting a tissue-destroying medium comprising a control unit (3) for controlling the medium transmission, and a transferring means (4), such as an electrode, which is connected to said main unit and adapted to be inserted into the predetermined volume for transferring the transmitted medium to the volume. The apparatus according to the invention is characterised in that it further comprises a measuring means (5–8) for measuring at least one optical characteristic of the predetermined volume, the optical characteristic varying with the size of the destroyed volume, the measuring means being connected to said control unit for controlling the supply of the tissue-destroying medium on the basis of the measured optical characteristic.

11 Claims, 2 Drawing Sheets

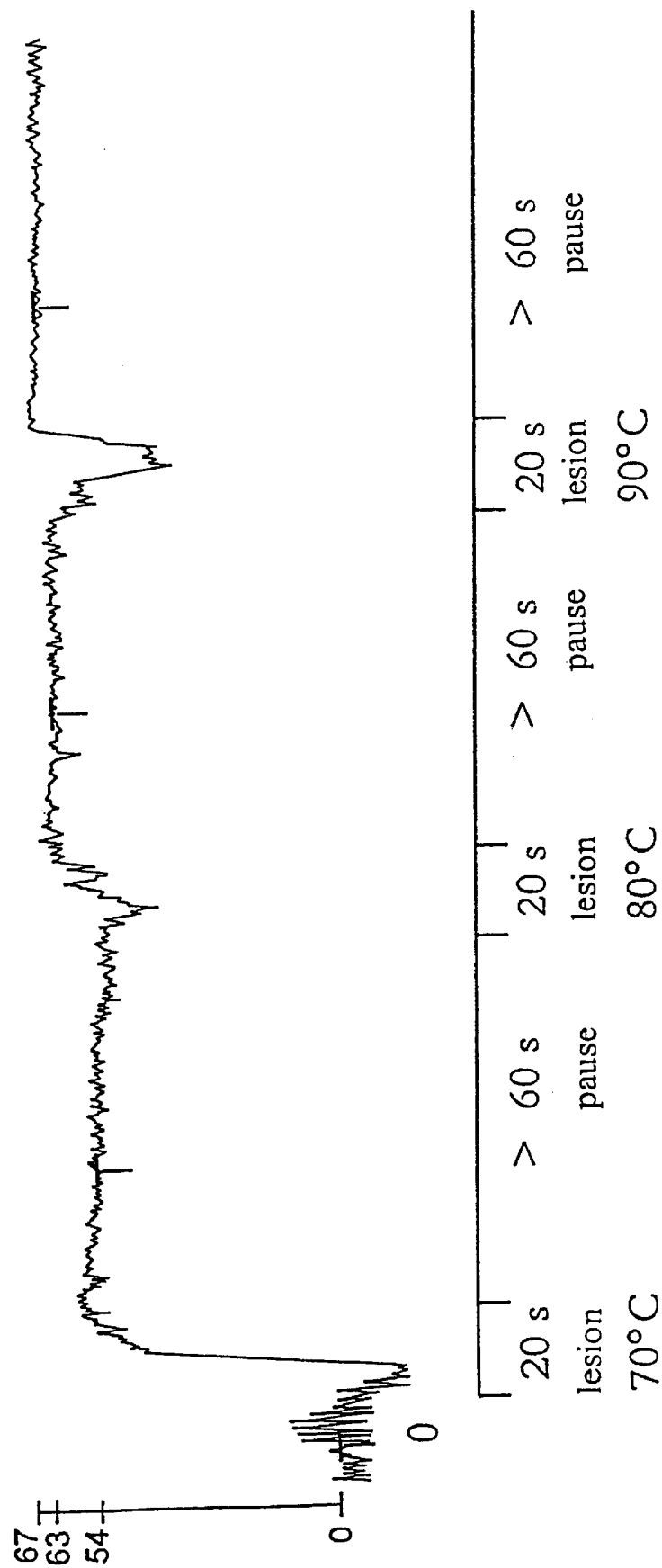

METHOD AND AN APPARATUS FOR CONTROLLED DESTRUCTION OF TISSUE

TECHNICAL FIELD

The present invention relates to an apparatus for destroying a predetermined defined volume in a tissue, such as generating controlled coagulation, so-called lesion, in the brain. More particularly, the apparatus comprises a main unit for transmitting a tissue-destroying medium comprising a control unit for controlling the medium transmission, and an-electrode which is connected to said main unit and adapted to be inserted into the predetermined volume for transferring the transmitted medium to the volume.

BACKGROUND

When treating certain diseases, the method is used to destroy a predetermined and well-specified area in a tissue. For instance, Parkinson's disease may be treated by controlled coagulation, so-called lesion, in the brain. This is carried out by an electrode being inserted into the specified area by using a stereotactic frame. Then a main unit which is connected to the electrode is set to supply a required high-frequency current to the specified area, heat being generated at the tip of the electrode and coagulation being provided. The main unit makes it possible to control current intensity, frequency, duration of treatment periods etc. An example of such a main unit is LEKSELL® NEURO GENERATOR, which is commercially available at Elekta Instrument AB in Sweden.

A problem with previously known equipment is, however, that it is difficult to control during treatment how large a volume is being destroyed. This implies that the setting of the equipment will be very complicated and require great skill and experience of the user. Thus, there is also a risk of the treatment not being as successful as it could be.

OBJECT OF THE INVENTION

It is thus an object of the present invention to provide an improved and more user-friendly apparatus where the above-mentioned disadvantages of previously known solutions entirely, or at least partly, are eliminated.

This object is achieved by means of an apparatus according to the appended claims.

BRIEF DESCRIPTION OF THE DRAWINGS

In the accompanying drawings

FIG. 3 is a schematic graph of the correlation between the relative change of an unprocessed Doppler frequency signal (RMS) and the time during a typical lesion generation.

DESCRIPTION OF PREFERRED EMBODIMENTS

Figure 1:
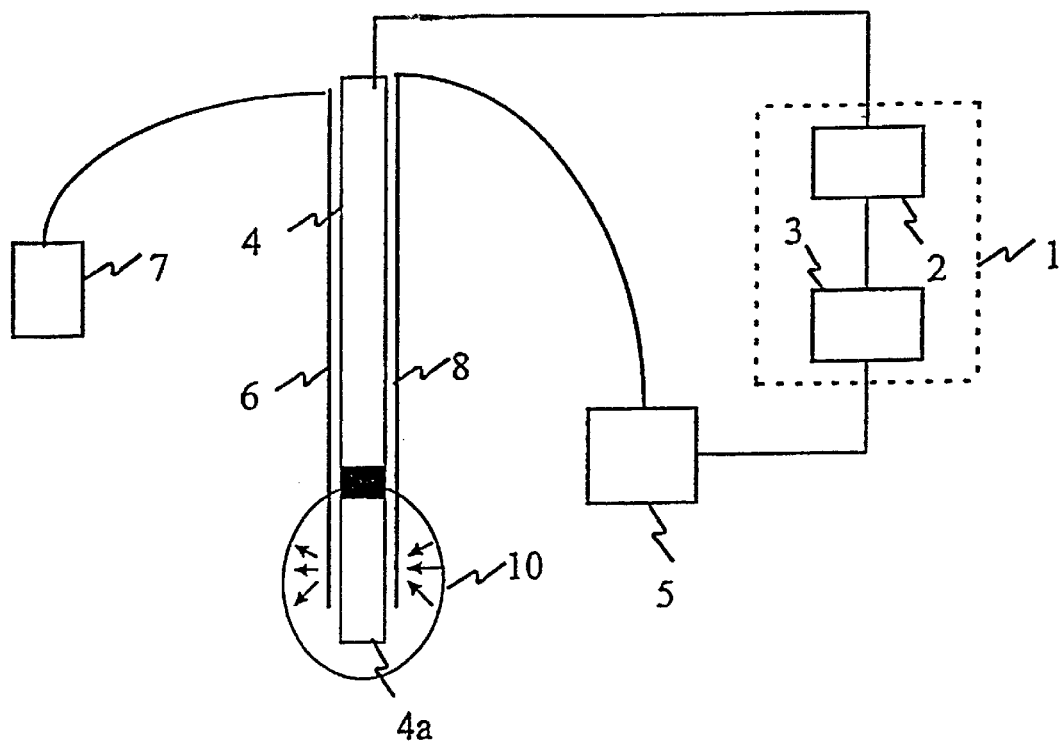
FIG. 1 is a schematic view of a first embodiment of an apparatus according to the invention.

The description will now be described in more detail by way of embodiments and with reference to the accompanying drawings;

The apparatus according to the invention comprises a main unit 1 for transmitting a tissue-destroying medium. This medium may, for instance, be high-frequency current which is generated in a generator 2 of the main unit and which, in the tissue, is transformed into heat and, thus, causes a lesion round the tip of the electrode 4a. However, other media are also possible, such as direct transmission of heat in the electrode, or transmission of laser light. Other destroying techniques are also conceivable, such as transmission of a refrigerating medium, transmission of a destroying chemical or the like.

The main unit further comprises a control unit 3 for controlling the medium transmission and, thus, for controlling how large a tissue volume 10 should be destroyed. If, for instance, high-frequency current is used as a medium, the control may take place with respect to current intensity, frequency, duration of treatment periods etc.

At least one electrode 4 is connected to the main unit and adapted to be inserted into the predetermined volume of tissue to be destroyed and to transfer the medium to this volume. The electrode may, for instance, be a monopolar or bipolar electrode for transmission of current, which is already used in equipment for lesion within neurosurgery.

Furthermore, the apparatus according to the invention comprises a measuring means for measuring at least one optical characteristic of the predetermined volume, the optical characteristic varying with the size of the destroyed volume of tissue. The measuring means is connected to said control unit 3 for controlling the supply of the tissue-destroying medium on the basis of the measured optical characteristic of the volume. Preferably, the measuring takes place continuously, the control being fed back. The optical characteristic is interpreted in connection with the control for an estimate of the destroyed volume of tissue. Preferably, either Doppler frequency or the absorption of the tissue is used as the optical characteristic. However, it might be possible to use other optical characteristics or a combination of optical characteristics for said control.

The measurement preferably takes place by light being sent into the volume of tissue, after which the reflected light is collected and interpreted. This is made, for instance, by the measuring means comprising a mesuring unit 5 and a measuring probe connected thereto. The measuring probe comprises a waveguide 6, such as a fibre-optical waveguide, for inserting light generated by a source of light 7 into the predetermined volume of tissue 10 and a return waveguide 8, such as another fibre-optical waveguide, for returning the reflected light to the measuring unit. The measuring unit 5 can then distinguish the optical characteristic from the reflected light. The source of light 7 is preferably a laser and, preferably, has a wavelength in the range of 600–900 nm. Especially, a wavelength in the red or infrared is desirable (630–800 nm) and, above all the infrared, since it gives a larger test volume. For instance, a HeNe laser can be used.

However, other sources of light may also be used within the scope of the invention, such as other lasers, spectrometers etc. It is also possible to use other wavelengths than those mentioned above, and instead of using one or a few wavelengths, wavelengths distributed within a range may also be used.

In particular, it is preferable to use Doppler-frequency measurements in connection with the present invention. This type of measurement gives a higher accuracy when measuring and also a stable zero level to start from, which is not possible when using previously known optical methods. Furthermore, this measuring method allows real-time detection for a defined volume. These characteristics are especially important for neurosurgery equipment because it is extremely important in this type of surgical operations that the destroyed volume of tissue be predetermined as exactly and reliably as possible since mistakes often result in very serious consequences.

In Doppler-frequency measurements especially the motion of the blood cells in the tissue is detected. The supplied light is reflected in the cell membrane and other interfaces of tissue with a refractive index which is different form that of the surroundings. Thanks to the internal motion, the reflected light contains time-dependent wave vectors depending on the generation of time-dependent phase factors in the individual occurring reflection diffusion. The motion leads to a Doppler-shifted frequency of the reflected light, and the size of the Doppler frequency depends on the extent of the blood circulation in the volume of tissue examined. It is previously known to estimate the microcirculatory flow of blood on the basis of a Doppler frequency, which is used, for instance, for measuring bleeding in the skin. For example, the commercially available detector equipment Periflux PF2 or PF3 from Perimed AD can be used for this purpose. However, this equipment is not intended for controlling additional equipment, but only for giving an estimate of the flow of blood. On the basis of the measured Doppler frequency, the concentration of movable blood cells within the measured volume, CMBC, can be estimated according to the following formula:

$$CMBC = k \left( \ln \left( 1 - \frac{1}{\eta^2 i_T} \int_{\omega_1}^{\omega_2} P(\omega) d\omega \right) \right)$$

wherein $P(\omega)$ is the spectral density of the Doppler signal, $\omega_1$ the low-frequency threshold, $\omega_2$ the high-frequency threshold, k is a constant, $\eta^2$ is an instrumental factor mainly depending on the optical coherence of the signal in the detector and $i_T$ is the total photo current. When heat is being supplied, the tissue is destroyed continuously or stepwise. Thus, also the internal motion in the tissue slows down, which decreases the size and the time variation of the phase factors of the reflected light. As is evident from the above expressions, the Doppler frequency will, thus, decrease as the micro-circulation decreases, which occurs concurrently with the destroyed volume of tissue spreading round the electrode.

Consequently, it is possible to distinguish successive phase transitions when destroying the tissue and also the size of the destroyed volume of tissue. It is thus possible to determine both the quality and the quantity of the tissue being destroyed during the process, and in accordance therewith control the equipment so that the desired destroyed volume of tissue and degree of destruction are obtained. This is carried out by recording the mean Doppler frequency as well as the amplitude or the magnitude of the Doppler signal. From a general point of view, the frequency indicates the quality, i.e. the degree of destruction, while the amplitude indicates the quantity, i.e. the size of the destroyed volume of tissue.

FIG. 3 shows a typical correlation between the relative change in an unprocessed Doppler-frequency signal (RMS) and the time for a typical lesion. The lesion typically occurs in short intervals of, for instance, 20 s, and with an increasing heat supply, and periods of rest of, for example, at least 60 s in between. From the signal, frequency as well as amplitude can be read. As is clearly evident, the result of the different occurrences of lesion differs from one another, both in the total signal change and in the signal change in the process. Thus, different stages in the solidification and the destruction of the tissue may be distinguished and identified.

Alternatively, the intensity of the reflected light can be measured. The reflected intensity, that is the signal intensity of the light signal which has been returned, is a measure of the absorption of the surrounding volume of tissue. As the tissue, for instance, coagulates, the colour of the tissue changes and turns darker and, thus, its absorption capacity increases.

The measuring probe is preferably connected to the electrode. This prevents further penetration of the tissue and, moreover, the measuring position will be fixed in relation to the electrode and, thus, the destroyed volume of tissue, thereby increasing the security of the measurement. FIG. 1 shows such an embodiment schematically. In this embodiment, two fibre-optical waveguides are placed on opposite sides of the electrode, one of them being used for emitting light in the volume of tissue and the other one for collecting and returning the diffused light. Alternatively, several waveguides may, however, be used, such as an entire bundle of waveguides arranged round the electrode. However, other types of positioning are also possible.

Figure 2:
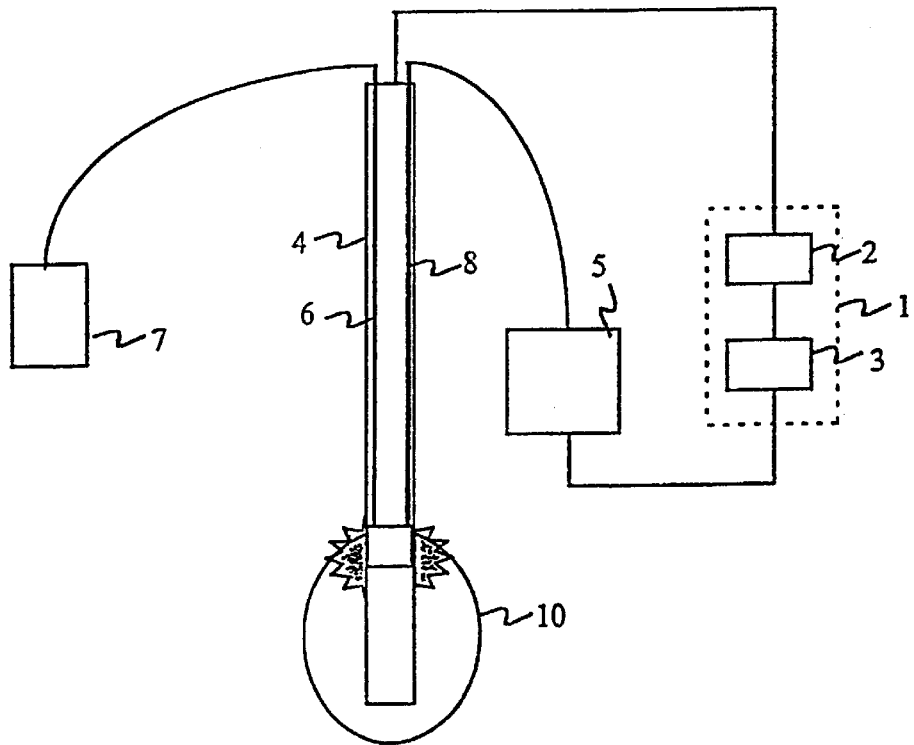
FIG. 2 is a schematic view of a second embodiment of an apparatus according to the invention.

Advantageously, the measuring probe can further be integrated in the electrode. This is shown schematically in FIG. 2. In this embodiment, the waveguides are extended inside the electrode and lead to the transparent openings in the lower part of the electrode. The openings may, for instance, be arranged in the insulating layer between the two polar areas in bipolar electrodes.

By means of the apparatus according to the invention, it is preferably feasible for the user to directly determine how large a volume of tissue should be destroyed. How the control should take place, that is how measured data from the measuring means should be interpreted by the control unit to obtain the correct volume, can be performed in different ways, which would be apparent for those skilled in the art. For instance, direct correlation between the measuring results of the measured characteristic and the volume of tissue can be established for different cases, such as different electrodes, different types of tissue etc. Alternatively, the control can take place on the basis of stored table results. The correlation between measuring results and volume can advantageously be measured in advance in a simulation environment. For instance, such measurements can be carried out in such a system as is disclosed in Applicant's Swedish patent application 9702462-4, where lesions are generated in absolution of protein, such as albumin. When producing such lesions in a test fluid, the volume and the extent of the lesion can be determined in time, for instance, by being calculated through filming with a video camera at the same time as the corresponding measurement as described above can be carried out. Thus, it is possible to relate measuring results to a predetermined volume size. Preferably, a relative control is used, the destruction of tissue being carried out until the signal of measuring results has changed to the desired degree, such as having been halved. However, it is naturally also possible to use absolute control, where tissue is destroyed until a certain predetermined level of measuring results is obtained.

The apparatus according to the invention is preferably intended for producing lesions in the brain for the treatment of, for instance, Parkinson's disease. However, the invention can also be applied in other apparatuses, such as ablation in hearts, in treatments by destroying a defined volume of tissue in the liver, the medulla oblongata, prostate and also in other tissues. One way of destroying the tissue may involve the supply of heat to the medium either directly or via high-frequency current, laser light or the like. Other media can, however, also be used, for other destroying techniques, such as cold or deadly chemical agents that acts locally.

Furthermore, the above apparatus has been described with a continuous, feed-back control. However, it is also possible to carry out measuring at certain occasions only, such as at regular intervals and, then, control on the basis of these measurements. The measuring means may also be designed differently, such as arranging the measuring probe spaced from the electrode. In cases where laser light is used for destroying the tissue, it may also be possible to measure directly on it and, thus, not supply additional light for the measurement. Such and other similar variants have to be considered to be comprised by the invention as defined by the appended claims.

What is claimed is:

1. An apparatus for destroying a predetermined defined volume in a tissue, the apparatus comprising:

a main unit for transmitting a tissue-destroying medium, the main unit comprising a control unit for controlling the medium transmission, and a transferring apparatus connected to the main unit and adapted to be inserted into the predetermined volume for transferring the transmitted medium to the predetermined volume;

measuring apparatus for measuring at least one optical characteristic of the predetermined volume, the at least one measured optical characteristic varying with a size of a destroyed volume of tissue, the measuring apparatus being connected to the control unit for controlling a supply of the tissue-destroying medium based on the at least one measured optical characteristic, the at least one optical characteristic including Doppler frequency, the measuring apparatus being adapted to calculate a concentration of movable blood cells in the predetermined volume based on the Doppler frequency and, based on the Doppler frequency, estimate the size of the destroyed volume.

2. An apparatus as claimed in claim 1, wherein the measuring apparatus is adapted to continuously measure the at least one optical characteristic of the predetermined volume during transmission of the medium.

3. An apparatus as claimed in claim 1, wherein the control unit is adapted to transmit medium adapted to cause controlled coagulation of the predetermined volume of tissue.

4. An apparatus as claimed in claim 3, wherein the control unit is adapted to transmit medium including high-frequency current.

5. An apparatus as claimed in claim 1, wherein the measuring apparatus comprises a measuring unit and a measuring probe connected thereto, the measuring probe including at least one waveguide for delivering light generated by a source of light to the predetermined volume and at least one return guide for returning reflected light to the measuring unit, the measuring unit being adapted to detect the at least one optical characteristic in the reflected light.

6. An apparatus as claimed in claim 5, wherein the source of light is a laser.

7. An apparatus as claimed in claim 5, wherein the measuring probe is connected to the transferring apparatus.

8. An apparatus as claimed in claim 1, wherein movable blood cells within the measured volume (CMBC) are substantially estimated according to:

$$CMBC = k\left(\ln\left(1 - \frac{1}{\eta^2 i_T}\int_{\omega_1}^{\omega_2} P(\omega)d\omega\right)\right)$$

wherein $P(\omega)$ is the spectral density of the Doppler signal, $\omega$ the low-frequency threshold, $\omega_2$ the high-frequency threshold, k is a constant, $\eta^2$ is an instrumental factor mainly depending on an optical coherence of a signal in the measuring unit and $i_T$ is a total photo current.

9. An apparatus as claimed in claim 1, wherein the apparatus is adapted to distinguish phase transitions of the predetermined volume based on the Doppler frequency during the transmission of the tissue-destroying medium.

10. An apparatus as claimed in claim 5, wherein the source of light is a laser and has a wavelength in the range of 600–900 nm.

11. An apparatus as claimed in claim 5, wherein the measuring probe is connected to the transferring apparatus and is integrated therewith.

* * * * *